US012606788B2

(12) United States Patent
Albagli et al.

(10) Patent No.: US 12,606,788 B2
(45) Date of Patent: Apr. 21, 2026

(54) PERFUSION FILTER MEMBRANE ASSEMBLY

(71) Applicant: Global Life Sciences Solutions USA LLC, Marlborough, MA (US)

(72) Inventors: Douglas Albagli, Marlborough, MA (US); William A. Hennessy, Marlborough, MA (US); Ralph Stankowski, Westborough, MA (US)

(73) Assignee: Global Life Sciences Solutions USA LLC, Marlborough, MA (US)

( * ) Notice: Subject to any disclaimer, the term of this patent is extended or adjusted under 35 U.S.C. 154(b) by 1024 days.

(21) Appl. No.: 17/464,589

(22) Filed: Sep. 1, 2021

(65) Prior Publication Data

US 2023/0065984 A1 Mar. 2, 2023

(51) Int. Cl.
| | |
|---|---|
| B01D 69/02 | (2006.01) |
| B01D 69/10 | (2006.01) |
| B01D 71/64 | (2006.01) |
| C12M 1/00 | (2006.01) |

(52) U.S. Cl.
CPC ............. C12M 29/04 (2013.01); B01D 69/02 (2013.01); B01D 69/10 (2013.01); B01D 71/64 (2013.01); C12M 23/14 (2013.01); C12M 23/26 (2013.01); C12M 29/10 (2013.01); *B01D 2325/02* (2013.01)

(58) Field of Classification Search
CPC ...... C12M 29/04; C12M 23/14; C12M 23/26; C12M 29/10; C12M 25/02; B01D 69/02;

B01D 69/10; B01D 71/64; B01D 2325/02; B01D 2313/025; B01D 2313/10; B01D 2313/20; B01D 63/087
See application file for complete search history.

(56) References Cited

U.S. PATENT DOCUMENTS

| | | | |
|---|---|---|---|
| 4,948,728 A | 8/1990 | Stephanopoulos et al. | |
| 5,139,946 A | 8/1992 | Howell et al. | |
| 5,693,537 A * | 12/1997 | Wilson ................... | C12M 23/34 |
| | | | 435/297.5 |
| 5,714,384 A | 2/1998 | Wilson et al. | |
| 6,368,592 B1 | 4/2002 | Colton et al. | |
| 8,580,560 B1 | 11/2013 | Ellis et al. | |

(Continued)

FOREIGN PATENT DOCUMENTS

| | | |
|---|---|---|
| EP | 0817834 A1 | 1/1998 |
| EP | 3356509 B1 | 7/2019 |

(Continued)

OTHER PUBLICATIONS

Search Report received in International Application No. PCT/EP2022/073787 dated Dec. 21, 2022, 4 pages.

(Continued)

*Primary Examiner* — Liban M Hassan
(74) *Attorney, Agent, or Firm* — Jeff B. Vockrodt; CM Law

(57) ABSTRACT

Filter holders and membranes are provided that can be included within a bioreactor bag system. The filter holders and membranes include features that allow incorporation of advanced membrane materials having differing material characteristics than traditional membranes that more closely matched the characteristics of the filter holder.

14 Claims, 11 Drawing Sheets

(56) References Cited

U.S. PATENT DOCUMENTS

| | | | |
|---|---|---|---|
| 9,017,997 B2 | 4/2015 | Wuenn et al. | |
| 10,464,064 B1 | 11/2019 | Wikswo et al. | |
| 10,532,324 B1 | 1/2020 | Masquelier et al. | |
| 10,752,874 B2 | 8/2020 | Johnson et al. | |
| 10,988,723 B1 | 4/2021 | Hatch et al. | |
| 11,027,239 B2 | 6/2021 | Zhang et al. | |
| 2004/0029266 A1 | 2/2004 | Barbera-Guillem | |
| 2004/0194440 A1* | 10/2004 | Bruck | F01N 13/009 |
| | | | 55/487 |
| 2006/0263873 A1 | 11/2006 | Levine et al. | |
| 2010/0221838 A1 | 9/2010 | Burgess et al. | |
| 2011/0212493 A1 | 9/2011 | Hirschel et al. | |
| 2011/0250585 A1 | 10/2011 | Ingber et al. | |
| 2013/0196375 A1 | 8/2013 | Strobbe | |
| 2014/0178992 A1 | 6/2014 | Nakashima et al. | |
| 2015/0004686 A1 | 1/2015 | Goral et al. | |
| 2017/0216744 A1* | 8/2017 | Kondo | C12M 47/02 |
| 2018/0326417 A1 | 11/2018 | Wikswo et al. | |
| 2018/0346864 A1* | 12/2018 | Faldt | C12M 23/14 |
| 2019/0105609 A1 | 4/2019 | Zhang et al. | |
| 2019/0134568 A1 | 5/2019 | Roy | |
| 2019/0330579 A1 | 10/2019 | Guenat et al. | |
| 2019/0336971 A1 | 11/2019 | Wikswo et al. | |
| 2020/0071657 A1 | 3/2020 | Johnson et al. | |
| 2020/0181555 A1 | 6/2020 | Hinojosa et al. | |
| 2020/0231921 A1 | 7/2020 | Zhang et al. | |
| 2020/0354668 A1 | 11/2020 | Sawyer et al. | |
| 2021/0069648 A1 | 3/2021 | Bransby et al. | |
| 2021/0205810 A1 | 7/2021 | Haun et al. | |
| 2021/0308628 A1 | 10/2021 | Hennessy et al. | |
| 2021/0308634 A1 | 10/2021 | Hennessy et al. | |
| 2022/0111338 A1 | 4/2022 | Stankowski et al. | |
| 2022/0314174 A1 | 10/2022 | Albagli et al. | |
| 2023/0272321 A1 | 8/2023 | Maoz et al. | |
| 2024/0002898 A1 | 1/2024 | Doryab et al. | |

FOREIGN PATENT DOCUMENTS

| | | |
|---|---|---|
| KR | 20060019241 A | 3/2006 |
| WO | 0141905 A1 | 6/2001 |
| WO | 2012158108 A1 | 11/2012 |
| WO | 2015034416 A1 | 3/2015 |

OTHER PUBLICATIONS

Search Report received in International Application No. PCT/EP2022/073789 dated Dec. 21, 2022, 4 pages.

Written Opinion received in International Application No. PCT/EP2022/073787 dated Dec. 21, 2022, 18 pages.

Written Opinion received in International Application No. PCT/EP2022/073789 dated Dec. 21, 2022, 18 pages.

* cited by examiner

PERFUSION FILTER MEMBRANE ASSEMBLY

BACKGROUND OF THE INVENTION

The bio-processing industry has traditionally used stainless steel systems and piping in manufacturing processes for fermentation and cell cultivation. These devices are designed to be steam sterilized and reused. Cleaning and sterilization are however costly labor-intensive operations. Moreover, the installed cost of these traditional systems with the requisite piping and utilities is often prohibitive. Furthermore, these systems are typically designed for a specific process, and cannot be easily reconfigured for new applications. These limitations have led to adoption of a new approach over the last ten years—that of using plastic, single-use disposable bags and tubing, to replace the usual stainless steel tanks.

In particular bioreactors, traditionally made of stainless steel, have been replaced in many applications by disposable bags which are rocked to provide the necessary aeration and mixing necessary for cell culture. These single-use bags are typically provided as sterile units and eliminate the costly and time-consuming steps of cleaning and resterilization. The bags are designed to maintain a sterile environment during operation thereby minimizing the risk of contamination.

One of the successful disposable bioreactor systems uses a rocking table on which a bioreactor bag is placed. The bioreactor bag is partially filled with liquid nutrient media and the desired cells. The table rocks the bag providing constant movement of the cells in the bag and also efficient gas exchange from the turbulent air liquid surface. The bag, typically, has at least one gas supply tube for the introduction of air, carbon dioxide, nitrogen or oxygen, and at least one exhaust gas tube to allow for the removal of respired gases. Nutrients can be added through other tubes.

During cultivation, the cells produce waste e.g. metabolites, ammonium ions and lactate, which have an inhibitory effect on cells. This effect becomes an issue particularly in cultivation at high cell densities, which are required for cost-effective production of biopharmaceuticals such as therapeutic proteins or virus antigens. One way to reduce the concentrations of inhibitory metabolites is to use perfusion cultivation where culture medium is bled off by hydraulic flow through a filter which retains the cells but lets the metabolites and proteins pass through the filter. Expressed proteins can then be recovered from the filtrate and fresh culture medium is continuously supplied to the bioreactor to compensate for the lost liquid. Perfusion filters can typically be installed in the interior of a bioreactor (or outside).

Perfusion filters may be incorporated into a bioreactor bag in several ways. One way to provide a perfusion filter to a disposable bioreactor is to provide the perfusion filter to a device comprising a screen and having a connector for attaching a tube for retrieving filtrate, often waste, and just let the device with a filter and screen float within the bioreactor. Another way to provide a perfusion filter has been described in U.S. Pat. No. 9,017,997. Here it is described that the perfusion filter is attached to the bottom of the bioreactor bag. WO2012/158108 and WO2015/034416 describe flexible bags for cell culture provided with internal filters attached to the wall of the bag by a filter holding device, adapted to maintain a distance between the filter and the wall of the bag.

EP 3 356 509 B1 describes a filter holding device that can be used within a bioreactor bag. FIG. 1A shows schematically a cross section side view of the filter holding device 101. The filter holding device 101 is provided in a flexible bag 103. The filter holding device 101 is suitably a flat or somewhat curved plate. The filter holding device 101 comprises some kind of distancing means on one side of a middle part 105 of the filter holding device. This distancing means could be for example ribs or a screen or some other kind of structure. The distancing means is provided on the side of the filter holding device to which a filter 107 should be attached. In this description the word filter is used but it could also be a membrane or a bioprocessing separation device used to retain or refrain.

A distancing means in the form of ribs are further shown and described in relation to FIG. 1B, which shows a schematic bottom view of the filter holding device shown in FIG. 1A. In this view the filter sealing area 109 can be seen to enclose the distancing means, here in the form of ribs 131. All the ribs are given the same numbers. The configuration and number of the ribs could vary. The function of the ribs is to hold the filter and distance the filter from the other side of the filter holding device such that the fluid can be filtered through the filter and drawn out through the opening 113 and port 111.

The filter holding device 101 comprises further a filter sealing area 109 provided around the distancing means. The filter sealing area 109 is arranged to be sealed to a periphery of the filter 107 to be held by the filter holding device. The filter will then be covering the distancing means when it has been sealed to the filter sealing area 109 of the filter holding device. In one embodiment the filter can also be sealed to one or more areas of the distancing means in order to prevent the filter from slacking. Furthermore, the filter holding device comprises a port 111 arranged around an opening 113 in the filter holding device 101, which opening connects fluidically with the spaces between the ribs. Said port 111 is arranged to be connected to a tube 115 for retrieving filtrate, usually waste. The port 111 and opening 113 are in one embodiment of the invention provided in the middle of the filter holding device 101 and centered inside the filter sealing area 109. However, the port and opening can also be provided in another position but they still need to be provided within the filter sealing area 109.

The flexible bag is shown here placed in a rocker tray 117. Attaching means are provided to the filter holding device for attaching the filter holding device to an inner surface of the flexible bag such that the at least one filter held by the filter holding device is provided at a distance from the inner surface of the flexible bag. In this embodiment of the invention the attaching means are provided as four openings 119a-d (only 119a and 119b can be seen) in the filter holding device and four stand-offs 121a-d to be received in the openings. Each one of the stand-offs 121a-d is attached one to each opening 119a-d in the filter holding device in a suitable way for example by heat sealing or my mechanical retention. The stand-offs 121a-d are then attached to the flexible bag inner surface for example by heat sealing or mechanical retention. In this embodiment the stand-offs 121a-d are shown to be attached to the bottom wall of the flexible bag 103 but they could as well be attached to another wall. Another possibility would also be that the stand-offs are molded together with the filter holding device. The number of openings and stand-offs and their positions could be varied. The height of the attaching means which in this shown embodiment are the standoffs, should be adapted for assuring that there will be a suitable distance between the filter and the bag inner surface for letting fluid flow between the filter and the bag surface and thereby create a crossflow effect over the filter, also called tangential flow. This tangential flow or crossflow over the filter will prevent fouling and clogging and will increase the life time of the filter. In another embodiment the attaching means is in the form of sealing two opposite sides of the filter holding device to the inner surface of the flexible bag. In order to provide a passage or channel for the fluid to pass between the filter and the bag surface the filter holding device needs to be bent or curved in some way.

The filter holding device 101 further comprises two deflector areas 123a, 123b. These deflector areas 123a, 123b are provided on opposite sides of the filter holding device and outside the filter sealing area 109. The deflector areas 123a, 123b are angled in relation to the rest of the filter holding device and they are pointing away from the inner surface of the flexible bag to which the filter holding device is attached when the filter holding device is mounted to the flexible bag. The deflector areas 123a, 123b affects the fluid flow in the flexible bag. The rocking tray is moved in a specific pattern such that the fluid inside the flexible bag is moving back and forth in a wave like motion. The deflector areas 123a, 123b will direct and force more fluid to pass between the filter and the bag surface to which the filter holding device is attached. Thereby a crossflow effect over the filter is created which will reduce clogging and fouling.

The present inventors have perceived a need to improve on filter membranes and filter holding assemblies in order to incorporate membrane filters made by more advanced membrane production techniques that incorporate materials having different characteristics than the typical materials utilized in filter holders used within bioreactor bags. Accordingly, the present invention seeks to improve microporous membranes and filter assemblies for holding those membranes.

SUMMARY OF THE INVENTION

In another aspect, the invention involves a filter assembly comprising: (1) a support plate; and (2) a filter membrane, the filter membrane comprising a porous filter region, the porous filter region comprising a plurality of pores having a minimum dimension of less than 100 microns; and a support region, where the support region comprises at least one support structure; (3) an underdrain seal abutting the filter membrane; and (4) an underdrain plate adapted to engage with the support plate and secure the perfusion filter membrane and underdrain seal in the perfusion filter assembly.

The support structure may comprise a plurality of membrane support holes, the membrane support holes having a minimum dimension greater than the minimum dimension of the pores. The filter membrane may have a membrane frame, the membrane frame comprising a plurality of frame support holes, the frame support holes being aligned with the membrane support holes. The membrane frame may have a different thickness and/or material composition than the filter membrane and engaging with the support region of the filter membrane. Alternatively, the filter membrane may comprise a membrane frame having the same material as the membrane with a different thickness. The filter membrane may comprise a membrane frame having a different material than the membrane. The membrane frame may have a plurality of frame support holes.

In one aspect, the underdrain plate and the support plate may be engaged with each other by a plurality of posts, and the support structure comprises a plurality of support holes that allow the plurality of support posts to pass through and engage with the plurality of support holes to secure the filter membrane within the filter assembly. The underdrain plate and the support plate may be engaged with each other by bonding wherein the underdrain plate and support plate include a recessed region for engaging with the support structure of the filter membrane and securing the filter membrane within the filter assembly. The filter membrane may be a polyimide filter membrane comprising a porous filter region, the porous filter region comprising a plurality of pores; and a support region, where the support region comprises a plurality of membrane support holes, the membrane support holes having a minimum dimension greater than the minimum dimension of the pores.

In another aspect, the invention may include a flexible bag bioreactor comprising: an inner surface and an outer surface; and a filter assembly, the filter assembly comprising: (1) a support plate; (2) a filter membrane, the filter membrane comprising: a porous filter region, the porous filter region comprising a plurality of pores having a minimum dimension of less than 100 microns; and a support region, where the support region comprises at least one support structure; (3) an underdrain seal abutting the filter membrane; and (4) an underdrain plate adapted to engage with the support plate and secure the perfusion filter membrane and underdrain seal in the perfusion filter assembly, wherein the filter assembly is attached to the inner surface of the flexible bag such that the filter membrane held by the filter assembly is provide at least a distance from the inner surface of the flexible bag.

In one aspect, the invention involves a filter membrane comprising a porous filter region, the porous filter region comprising a plurality of pores having a minimum dimension of less than 100 microns; and a support region, where the support region comprises at least one support structure. The support structure may comprise a plurality of membrane support holes, the membrane support holes having a minimum dimension greater than the minimum dimension of the pores. The filter membrane may also have a plurality of standoff holes (e.g., four standoff holes).

The filter membrane may include a pore free region between the support holes and the porous filter region. The pore free region may surround several of the support holes. Alternatively, each of the support holes may be surrounded by a pore free region, and the pore region surrounds each of the support holes and corresponding pore free region.

The filter membrane may have a thickness in the range of 5 to 25 microns. The pores may have an aspect ratio ranging from 0.5:1 to 20:1. The pores may have a minimum dimension of 20 nm.

In another aspect, the invention involves a polyimide filter membrane comprising a porous filter region, the porous filter region comprising a plurality of pores; and a support region, where the support region comprises a plurality of membrane support holes, the membrane support holes having a minimum dimension greater than the minimum dimension of the pores.

DETAILED DESCRIPTION OF THE INVENTION

Figures 1A, 1B:
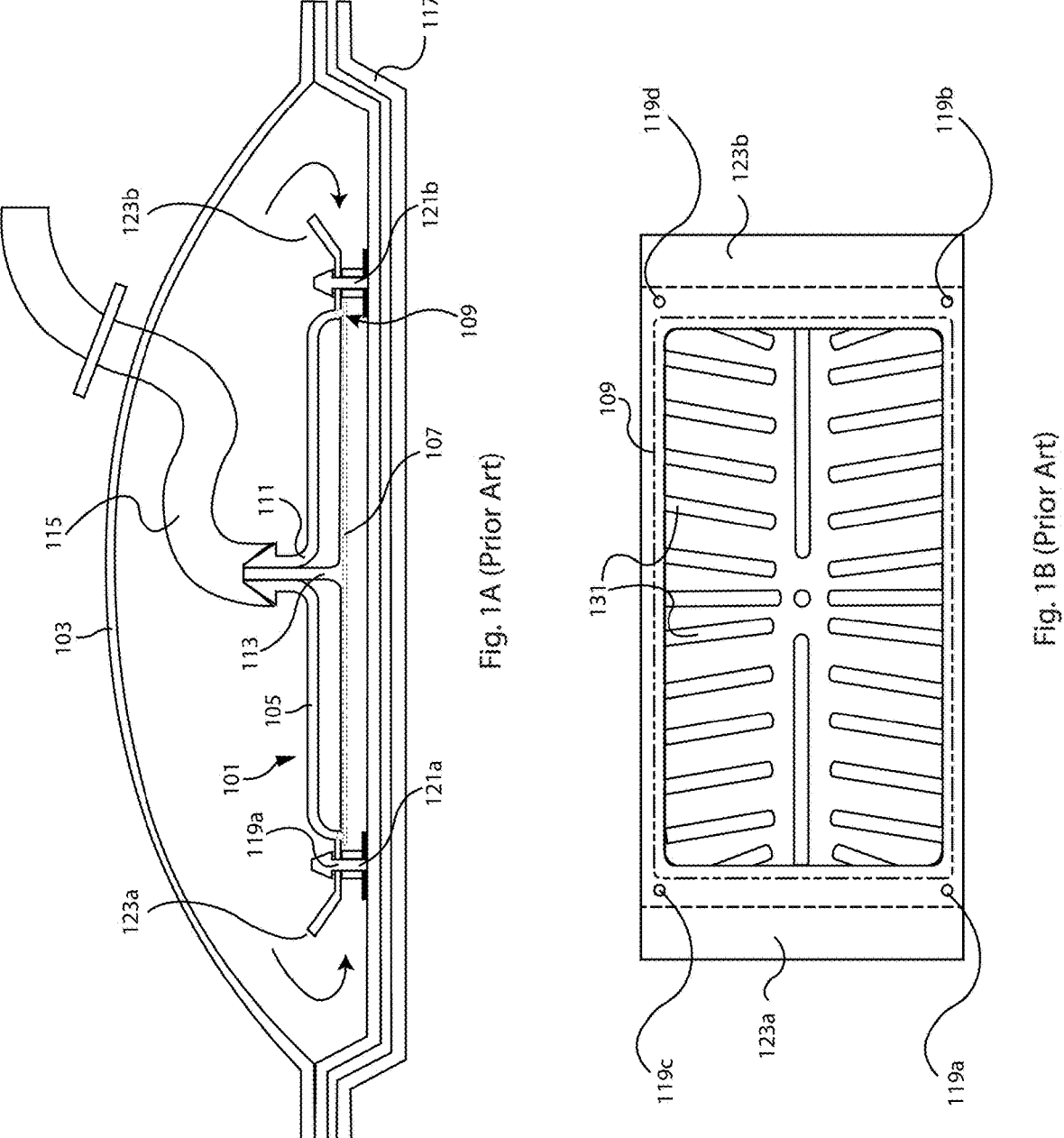
FIG. 1A shows a prior art perfusion filter assembly.
FIG. 1B shows a first view of a portion of the prior art filter assembly shown in FIG. 1A.

The present invention involves perfusion filter assemblies and filer membranes for use in those perfusion filter assemblies. The perfusion filter assemblies and perfusion membranes disclosed herein are particularly adapted to membranes that are made with advanced processes, such as photolithography and etching. The present inventors have found that membranes made according to these processes have material characteristics that make them unsuitable for use with traditional perfusion filter assemblies. For example, polyimide membranes can be difficult to bond to the polyethylene components used in perfusion filter assemblies, including perfusion filter bags. The filter membranes and filter assemblies disclosed herein include features that overcome one or more of these obstacles.

The forming of porous regions in a polymeric membrane according to one such advanced process is described in U.S. patent application Ser. No. 16/842,402, entitled "POROUS FLAT DEFORMATION-RESISTANT MEMBRANE"

which was filed Apr. 7, 2020, and Ser. No. 16/842,448, entitled "BIOCOMPATIBLE HIGH ASPECT-RATIO POROUS MEMBRANE" which was filed Apr. 7, 2020, each of which is incorporated by reference herein. These processes produce filter membranes according to steps shown in FIG. 2A. A membrane layer 102 is formed on the base layer 100. A hard mask layer 103 is formed on the polymer layer 102. And a photomask layer 104 is provided on the hard mask layer 103. The base substrate 100 may be made from glass, for example. Other suitable materials include silicon or metal. In one aspect, the membrane layer 102 and base 100 have a similar coefficient of thermal expansion such that a glass substrate and polyimide membrane layer is utilized.

Figure 2A:
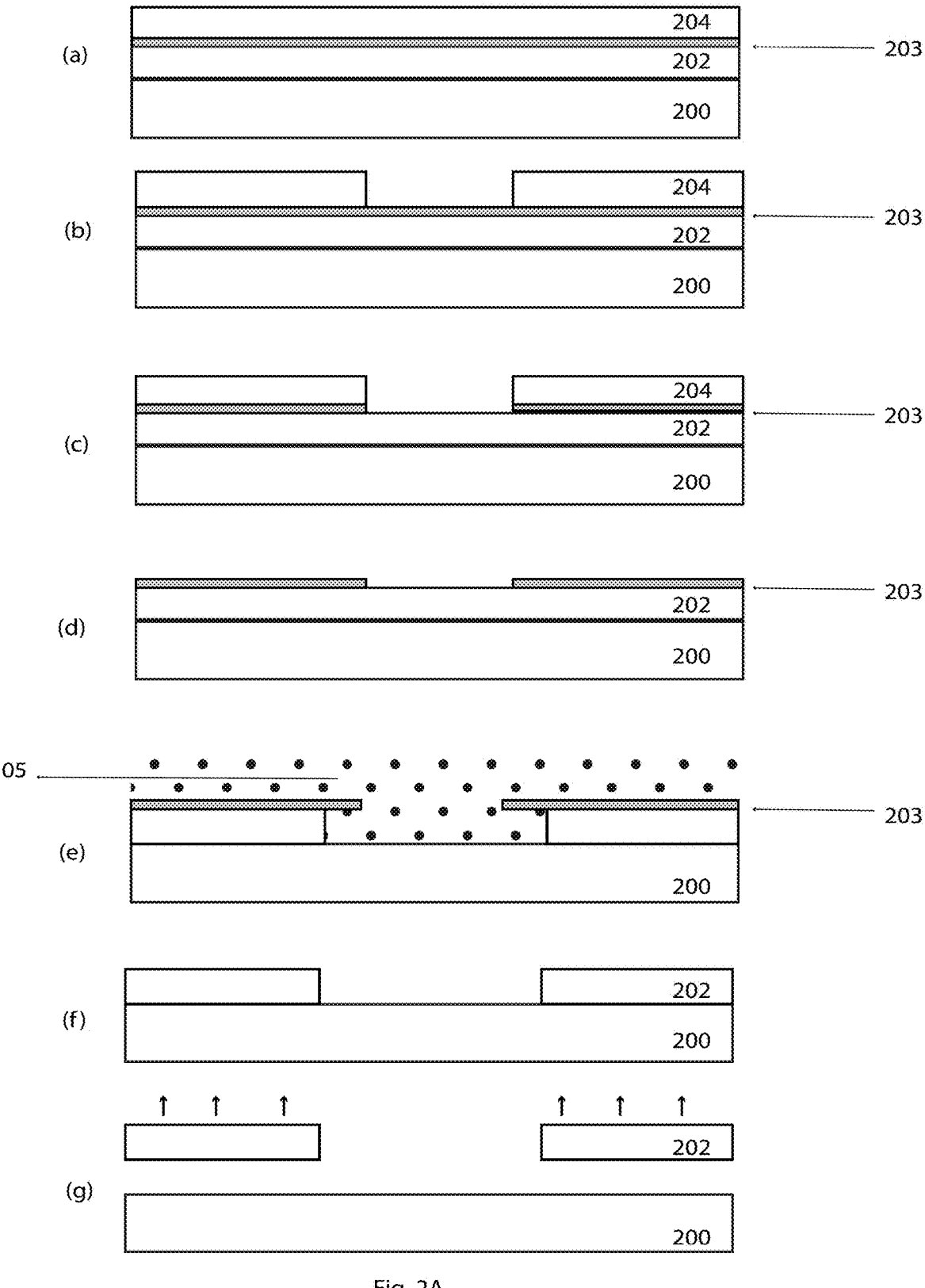
FIG. 2A shows a first process that can be utilized to make a perfusion filter membrane for use in a perfusion filter assembly, according to an embodiment of the invention.
Figure 2B:
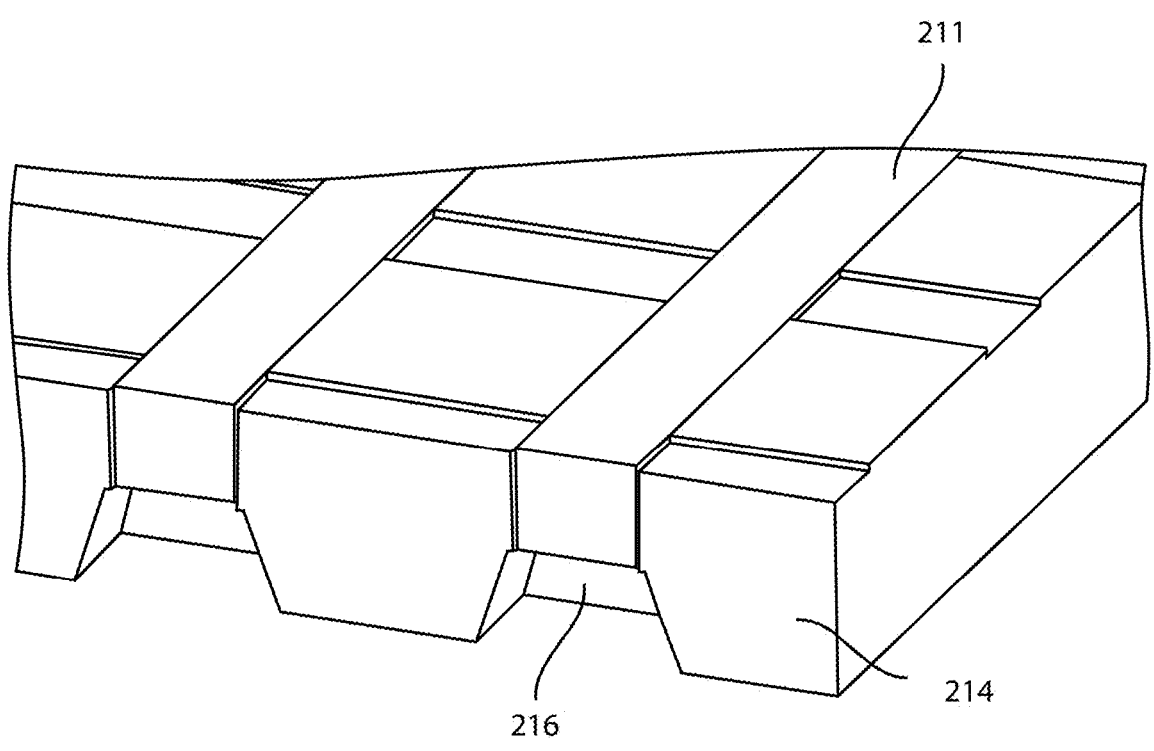
FIG. 2B shows a second process that can be utilized to make a perfusion filter membrane for use in a perfusion filter assembly, according to an embodiment of the invention.
Figure 2C:
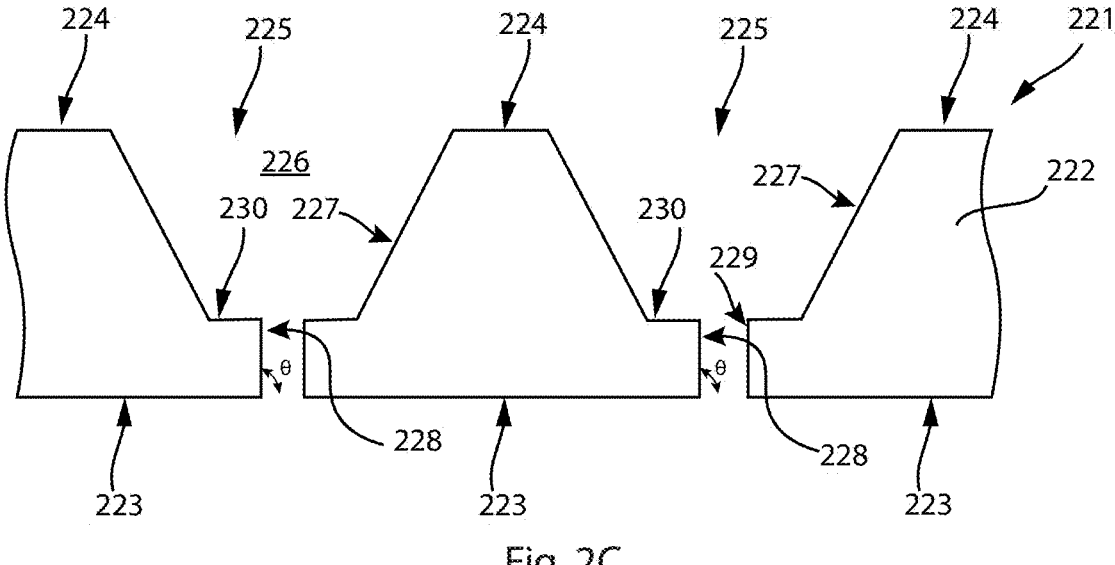
FIG. 2C shows a third process that can be utilized to make a perfusion filter membrane for use in a perfusion filter assembly, according to an embodiment of the invention.

The first step in making the membrane from the structure of FIG. 2(a) is to provide a patterned photoresist layer 104 by exposing the surface of the photoresist to a light pattern, and developing the photoresist to leave the photoresist pattern shown in FIG. 2(b). After forming the opening 101, the hard mask 103 is etched in the location of the opening 101 to form the hard mask opening 106 as shown in FIG. 2(c) and photoresist 104 is then removed as shown in FIG. 2(d). After etching the membrane layer 102 to form the membrane layer opening 107, the hard mask layer 103 should be removed as shown in FIG. 2(f). The removal of the hard mask layer 103 is desirably conducted in a manner that is selective relative to the membrane layer 102. After removal of the hard mask layer 103, the patterned membrane layer 102 is separated from the base layer 100 as shown in FIG. 2(g).

Another advanced method for making porous membrane is described in U.S. patent application Ser. No. 17/067,528, entitled "TANGENTIAL FLOW CASSETTE-HF EMULATION" and filed Oct. 9, 2020, which describes such polymeric membranes and techniques. One example of a filter membrane made according to this process is shown in FIG. 2B. These membranes include a plurality of first membrane material layer strips 101, a second membrane material 104 binding to each of the plurality of first membrane material layer strips, the second membrane material comprising a plurality of windows 106 exposing each of the first membrane material strips, wherein the biocompatible polymeric filtration membrane comprises pores defined by uniform passages defined by the first membrane material layer strips 101 and the second membrane material layer 104 that fluidically connect within each window 106. The uniform pore is formed by etching a sacrificial material layer (not shown) deposited on the first membrane material layer strips 101. These methods allow formation of pores having a minimum pore size defined by the thickness of a sacrificial layer. In many cases, the minimum dimension of pores made using this technique may range from 20 to 1000 nm. The thickness of membranes made according to these techniques preferably ranges from 2-10 microns.

Another advanced method for making porous membrane is described in U.S. patent application Ser. No. 17/219,428, entitled "MICROPORE MEMBRANES AND METHODS OF FABRICATION THEREOF USING PILLAR TEMPLATES," and filed Mar. 31, 2021, which describes such polymeric membranes and techniques. One example of a filter membrane made according to this process is shown in FIG. 2C. The porous membrane 101 is produced using a pillar template which allows for formation of a well-defined and reproducible exit dimension defined by the second region 108 when used in conjunction with photolithographic techniques performed on the polymeric layer 102 of the porous membrane 101. The polymer layer 102 of the membrane 101 has a bottom surface 103 and top surface 104. The plurality of pores 105 extend through the polymer layer 102. Each pore has a first region 106 with a tapered profile 107 that opens wider at the intersection of the top surface of the membrane 104, and a second region 108 with a substantially vertical profile 109 that intersects the bottom surface of the membrane 103. As shown in FIG. 2C, the tapered profile 107 may be a conical profile. The first region 106 intersects the second region 108 at an intermediate surface 110 exposed through the opening created by the first region 106. The intermediate surface 110 provides a buffer that allows for non-uniformity in the etching and formation of the first region among different pores in the same membrane, and between separate manufacturing runs of different membranes.

Figures 3A, 3B:
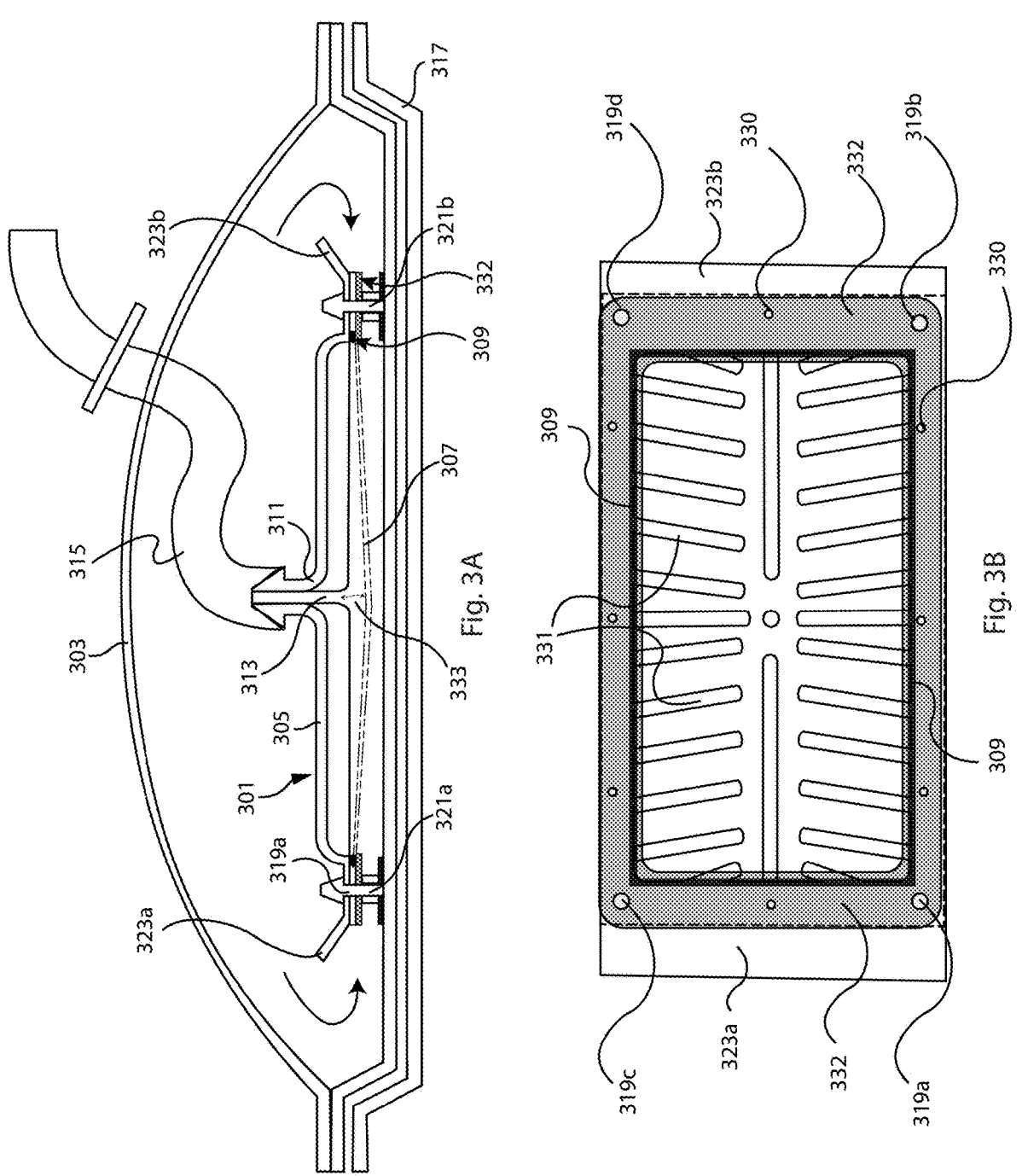
FIG. 3A shows a perfusion filter assembly utilizing a support frame with membrane support holes according to an embodiment of the invention.
FIG. 3B shows a bottom up view of the perfusion filter assembly of FIG. 3A with support frame.

FIGS. 3A-D show a perfusion filter membrane utilizing membrane support holes according to an embodiment of the invention. As shown in FIGS. 3A-B, a bioreactor bag 303 includes a filter holding device 301 having a middle part 305 and being placed at the bottom of the bioreactor bag 303 where the filter membrane 307 faces the bottom of the bioreactor bag 303. A port 311 allows filtered fluid to exit the bioreactor bag through opening 313 and out of the tube 315, where ribs 331 hold the filter and distance the filter from the other side of the filter holding device such that the fluid can be filtered through the filter and drawn out through the opening 313 and port 311. The filter holding device includes openings 319a-d which are used for attaching to standoffs 321a-d (only 321a and 321b are shown). The filter holding device 301 includes deflector areas 323 that improve the flow under the filter holding device 301 within the bioreactor bag 303. The bioreactor bag 303 may be placed on a rocker tray 317. The filter holding device 301 may be attached to the bottom of the bioreactor bag 303 using standoffs 321a-d (only 321a and 321b are shown) which correspond to holes 319a-d as seen in FIG. 3B.

Figure 3C:
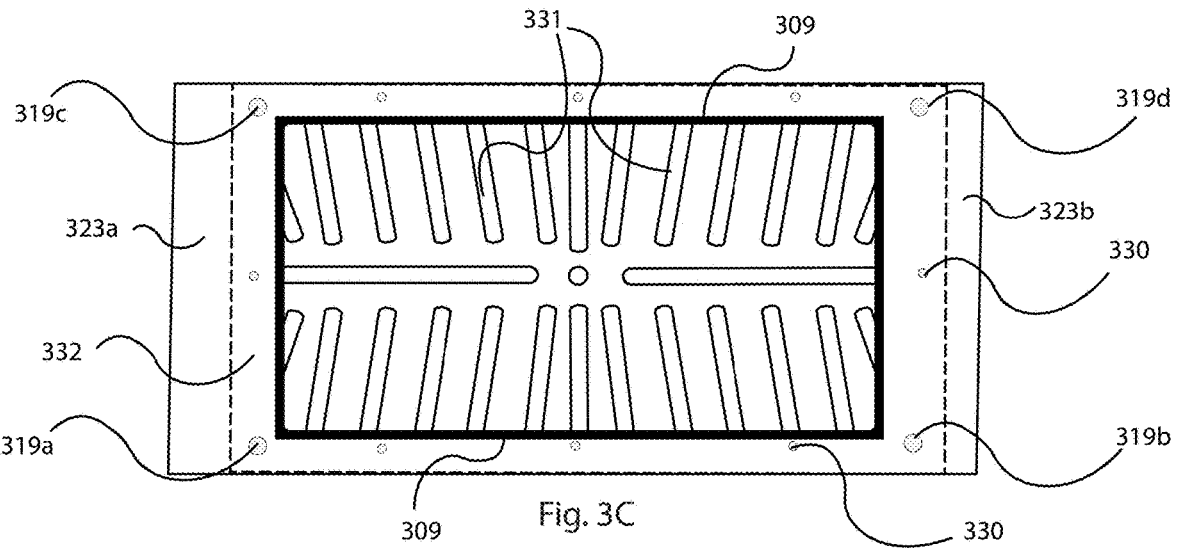
FIG. 3C shows a bottom up view of the perfusion filter assembly of FIG. 3A without support frame.
Figure 3D:
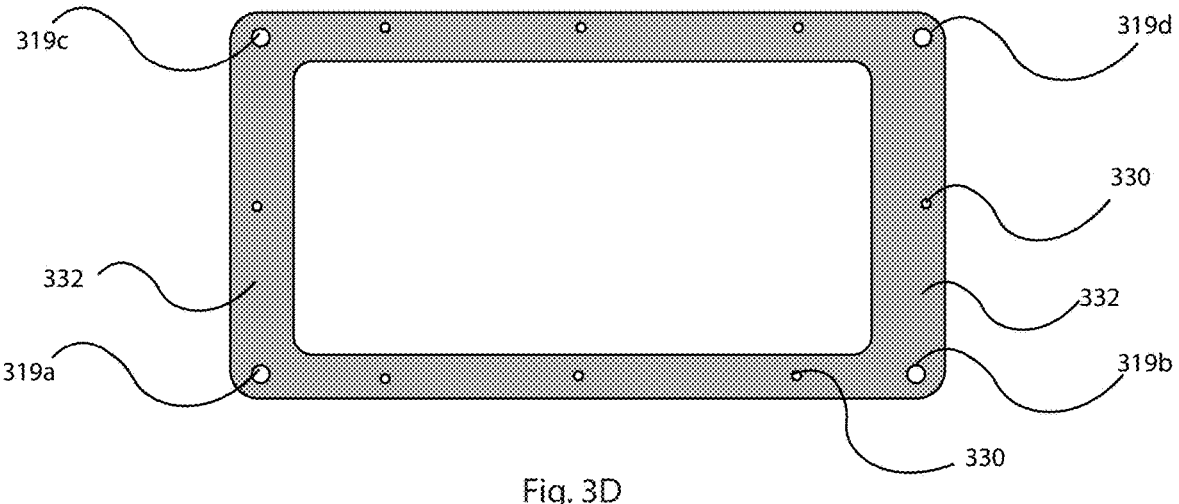
FIG. 3D shows the support frame of FIG. 3A.

The filter membrane 307 may be attached to the filter holding device 301 using the support structure, such as support frame 332 of FIG. 3D, and a seal 309. The seal 309 can be an O-ring made from a resilient material such as rubber as shown in FIG. 3C. The seal 309 is adapted to prevent liquid from leaking from the bioreactor bag past the filter membrane 307. The seal may be seated in a groove in the shape of the seal.

The support frame 332, may include support holes 330 where a pin or other structure may be used to further secure the support frame 332 a membrane 307 in place. The number of support holes 330 may depend on the materials and the use case. In the case where higher pressures are utilized, more support holes may be used. The support pins 330 may be threaded such that they may be screwed into the periphery of the filter membrane support. Although not necessary to seal the filter membrane 307 due to the seal 309, the support pins may be provided with seals or washers depending on the thickness of the membrane 307 and seal 309 and the need for compression.

Figures 4A, 4B:
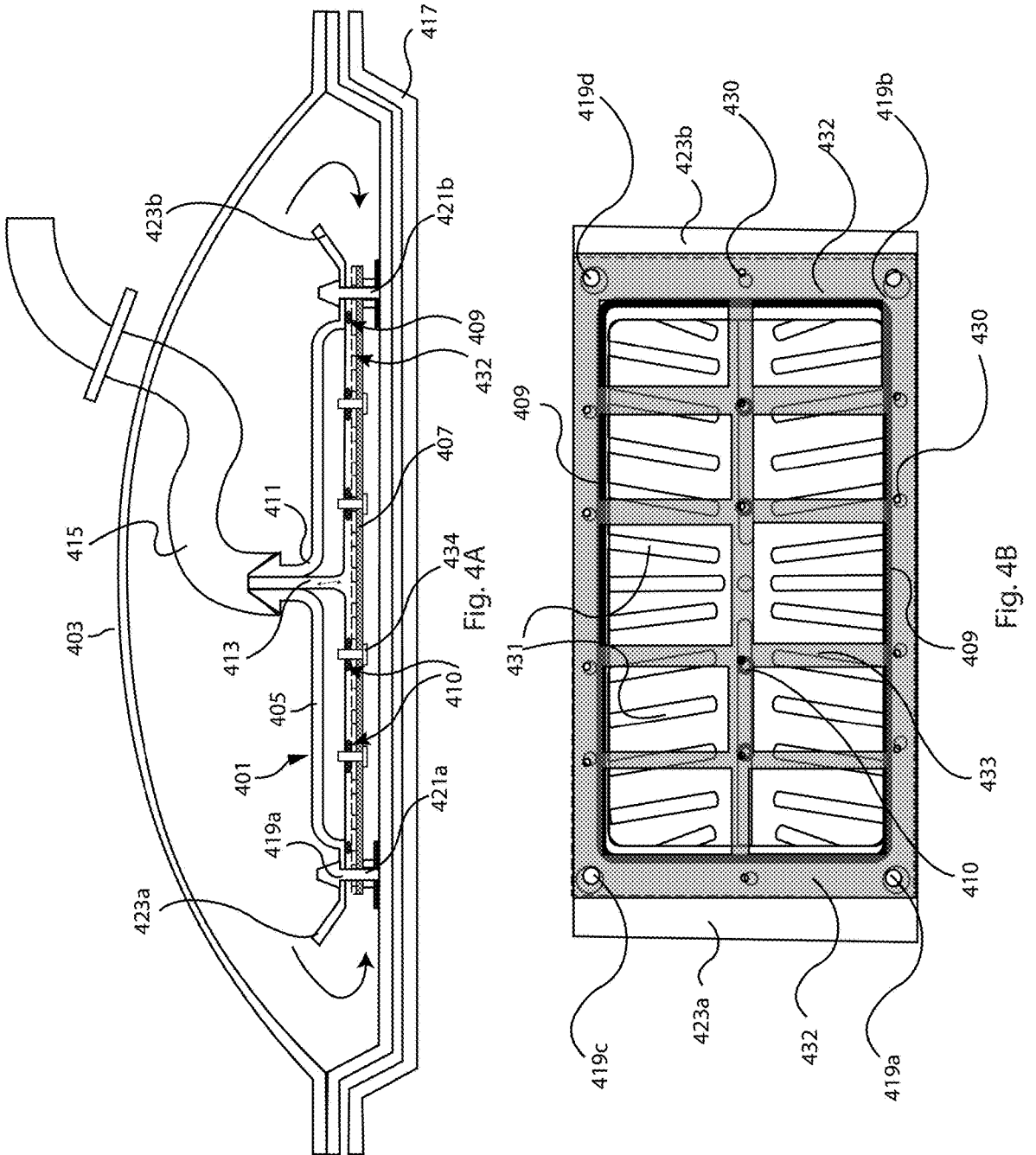
FIG. 4A shows a perfusion filter assembly utilizing a support frame with membrane support holes according to an embodiment of the invention.
FIG. 4B shows a bottom up view of the perfusion filter assembly of FIG. 4A with support frame.

FIGS. 4A-B show a perfusion filter assembly utilizing a support frame with membrane support holes according to an embodiment of the invention. As shown in FIGS. 3A-B, a bioreactor bag 403 includes a filter holding device 401 placed at the bottom of the bioreactor bag 403 where the filter membrane 407 faces the bottom of the bioreactor bag 403. A port 411 allows filtered fluid to exit the bioreactor bag through opening 413 and out of the tube 415. The filter holding device includes openings 419a-d which are used for attaching to standoffs 421a-d (only 421a and 421b are shown). The filter holding device 401 includes deflector areas 423 that improve the flow under the filter holding device 401 within the bioreactor bag 405. The bioreactor bag 405 may be placed on a rocker tray 417. The filter holding device 401 may be attached to the bottom of the bioreactor bag 403 using standoffs 421a-d (only 421a and 421b are shown) which correspond to holes 419a-d as seen in FIG. 4B.

The filter membrane 407 may be attached to the filter holding device 401 using the support structure, such as support frame 432, and a seal 409 as shown in FIG. 4B. The seal 409 can be an O-ring made from a resilient material such as rubber. The seal 409 is adapted to prevent liquid from leaking from the bioreactor bag past the filter membrane 407. The seal may be seated in a groove in the shape of the seal.

The support frame 432, may include support holes 430 where a pin or other structure may be used to further secure the support frame 432 a membrane 407 in place. The number of support holes 430 may depend on the materials and the use case. In the case where higher pressures are utilized, more support holes may be used. The support pins 430 may be threaded such that they may be screwed into the periphery of the filter membrane support. Although not necessary to seal the filter membrane 407 due to the seal 409, the support pins may be provided with seals or washers depending on the thickness of the membrane 407 and seal 409 and the need for compression.

The support frame 432 also include central support pins 434 that secure internal portions 433 of the frame 432 to the ribs 431 of the middle part 405 of the filter holding device. Each pin 434 preferably includes a seal 410 which can be an O-ring.

Figures 5A, 5B, 5C:
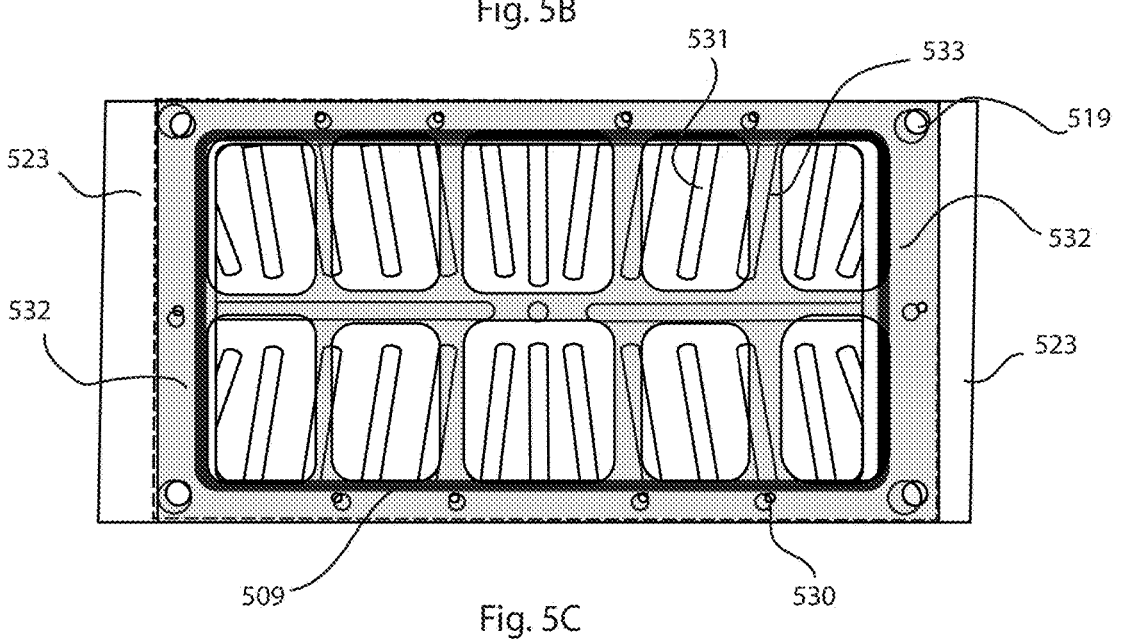
FIG. 5A shows a bottom up view of a perfusion filter assembly according to an embodiment of the invention.
FIG. 5B shows a support frame according to an embodiment of the invention.
FIG. 5C shows a bottom up view of the perfusion filter assembly of FIG. 5A with support frame.

FIG. 5A shows a bottom up view of a perfusion filter assembly according to an embodiment of the invention. Ribs 531 are provided to support the filter membrane (not shown). Holes 519 are used to support a standoff for supporting the device in place within the bioreactor bag as shown with previous images. The holes may further secure the filter membrane within the frame 532, 533, which is shown in FIG. 5B. Additional holes 530 are provided for posts to further anchor the membrane within the filter assembly. Seal 509 is further provided to prevent leakage around the filter membrane. The assembled filter assembly is shown in FIG. 5C.

Figure 6A:
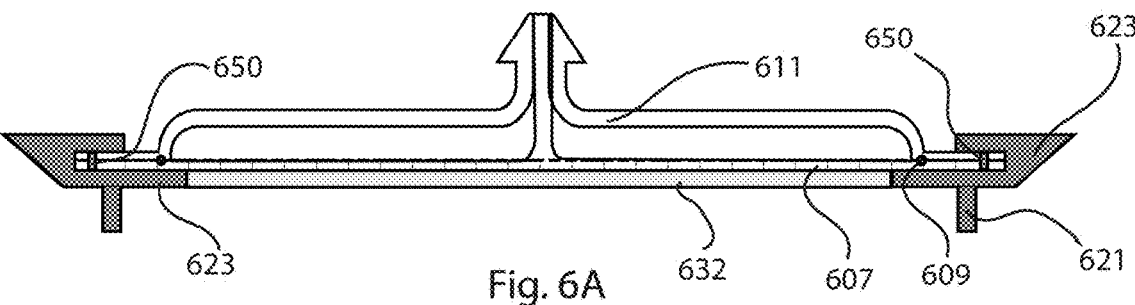
FIG. 6A shows a side view of a perfusion filter assembly and structure for securing the support frame and filter membrane according to an embodiment of the invention.

FIG. 6A-E show a side views of a perfusion filter assembly and various structures for securing the support frame and filter membrane according to an embodiment of the invention. The filter membrane 607 is positioned below a support plate 611 which may have ribs or other structures supporting the filter membrane 607. A frame 632 may be used to support the bottom of the filter membrane 607. Holders 623 may be used with standoffs 621 to hold the filter assembly in place and position it relative to a filter bag as previously described. A seal 609 is used to surround the filter membrane 607. In FIG. 6A, a post 650 is used to secure the support plate 611 and filter 607 within the assembly. The post 650 may be a compression fit or screw.

Figure 6B:
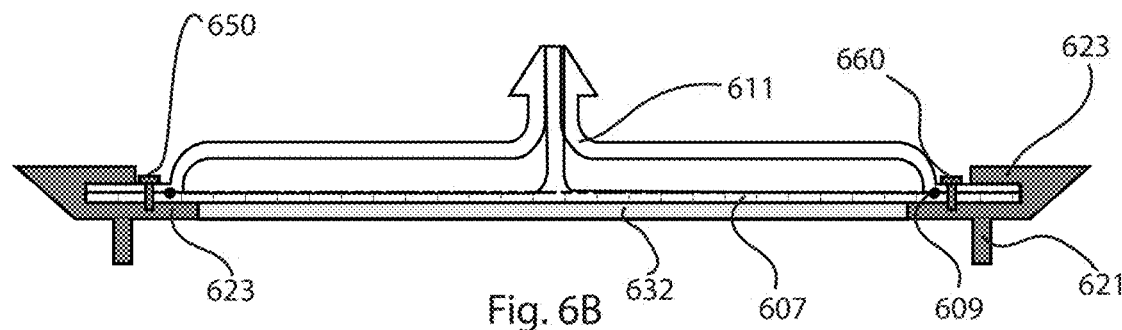
FIG. 6B shows a side view of a perfusion filter assembly and structure for securing the support frame and filter membrane according to an embodiment of the invention.
Figure 6C:
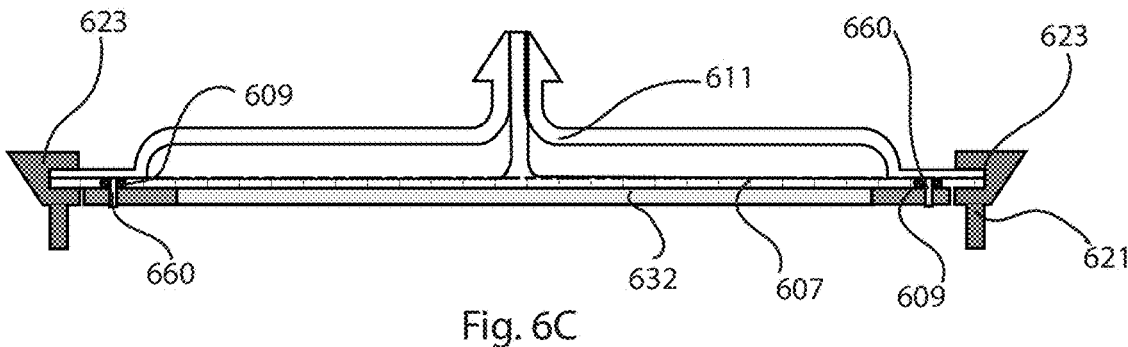
FIG. 6C shows a side view of a perfusion filter assembly and structure for securing the support frame and filter membrane according to an embodiment of the invention.

FIG. 6B shows a side view of a perfusion filter assembly and bolt 660 structure for securing the support frame and filter membrane according to an embodiment of the invention. The bolt may be threaded and secured by a hole with matching threads in the holder 623. FIG. 6C shows a side view of a perfusion filter assembly and pins 660 for securing the support frame and filter membrane according to an embodiment of the invention. The pins 660 may be integral with the support 611. The pins 660 may be adapted to interface with a bottom part of the holder 623 or the frame 632. This interface may be a compression fit.

Figure 6D:
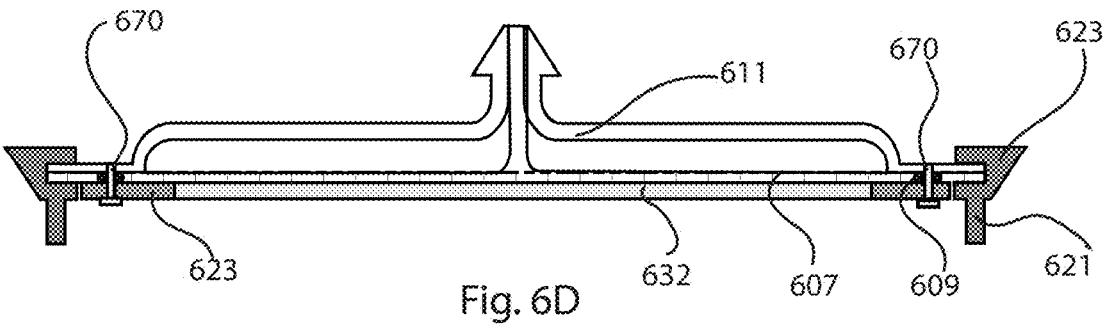
FIG. 6D shows a side view of a perfusion filter assembly and structure for securing the support frame and filter membrane according to an embodiment of the invention.
Figure 6E:
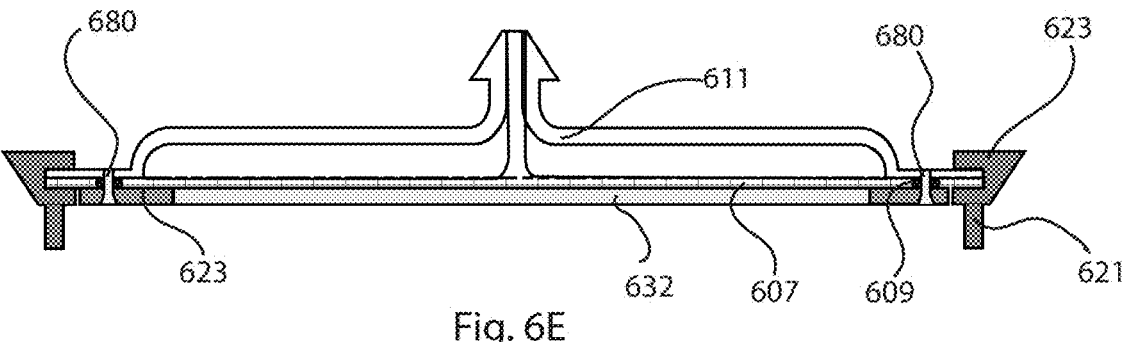
FIG. 6E shows a side view of a perfusion filter assembly and structure for securing the support frame and filter membrane according to an embodiment of the invention.

FIG. 6D shows a side view of a perfusion filter assembly and bolt 670 for securing the holder 623 frame, filter membrane 607, and support 611 according to an embodiment of the invention. The bolt 670 may be threaded, or may form a compression fit with the support 611. The bolt 670 can be put into place from the lower side which can be advantageous during assembly since the filter membrane 607 would typically be placed onto the support 611 followed by the frame 632 and holder 623. FIG. 6E shows a side view of a perfusion filter assembly and tapered pin 680 for securing the support frame and filter membrane according to an embodiment of the invention. The tapered pin may be threaded into the support 611 for securing the membrane 607.

Figure 7A:
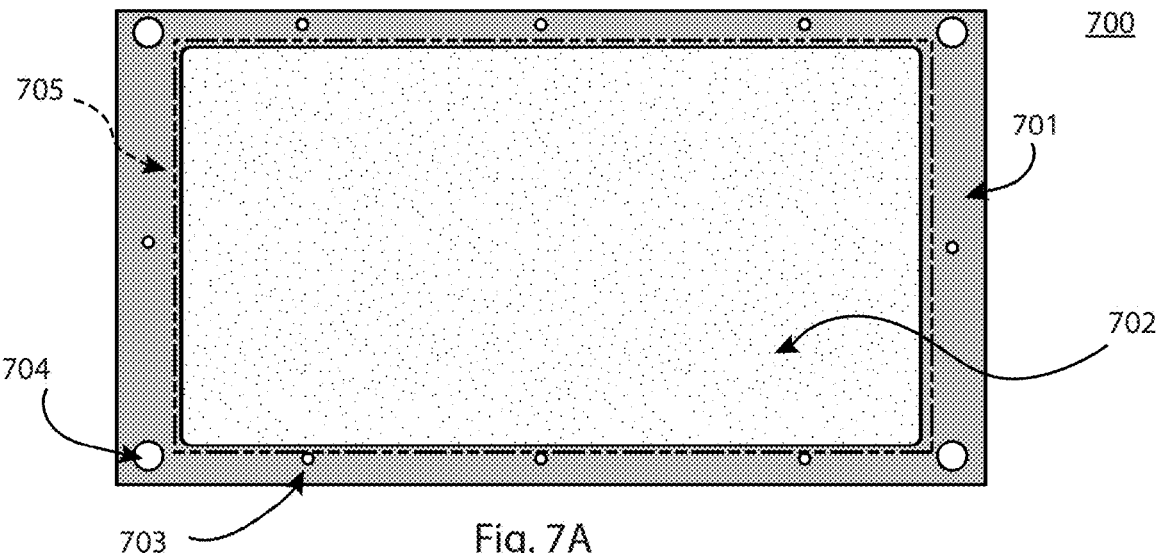
FIG. 7A shows a filter membrane in accordance with an embodiment of the invention.
Figure 7B:
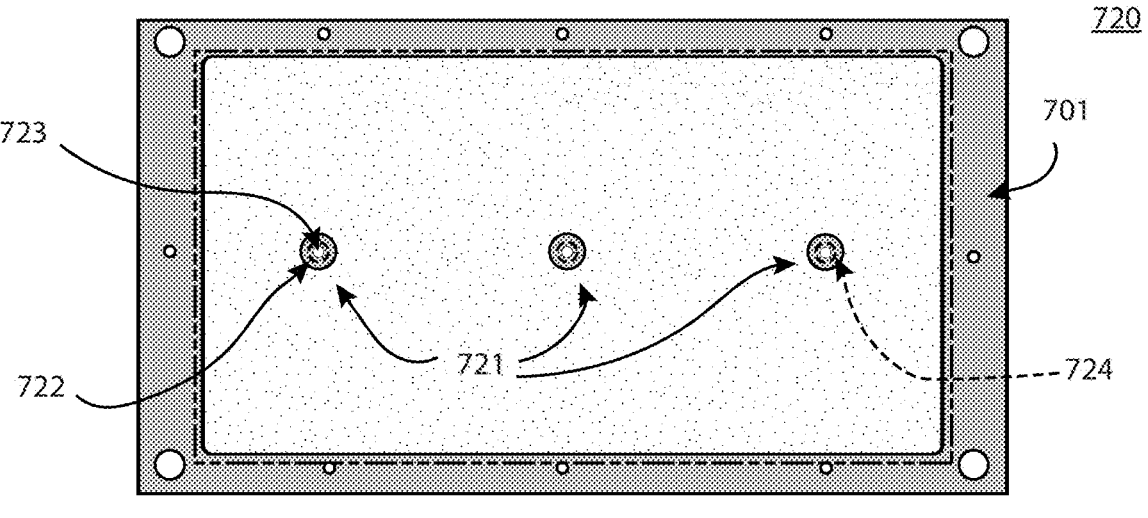
FIG. 7B shows a filter membrane in accordance with an embodiment of the invention.
Figure 7C:
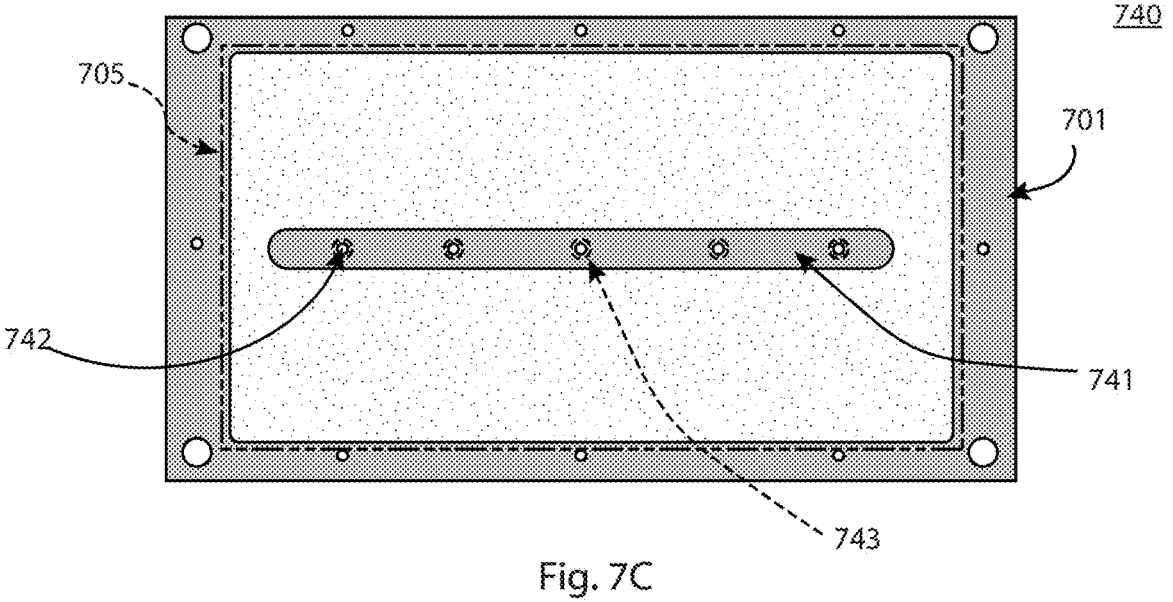
FIG. 7C shows a filter membrane in accordance with an embodiment of the invention.
Figure 7D:
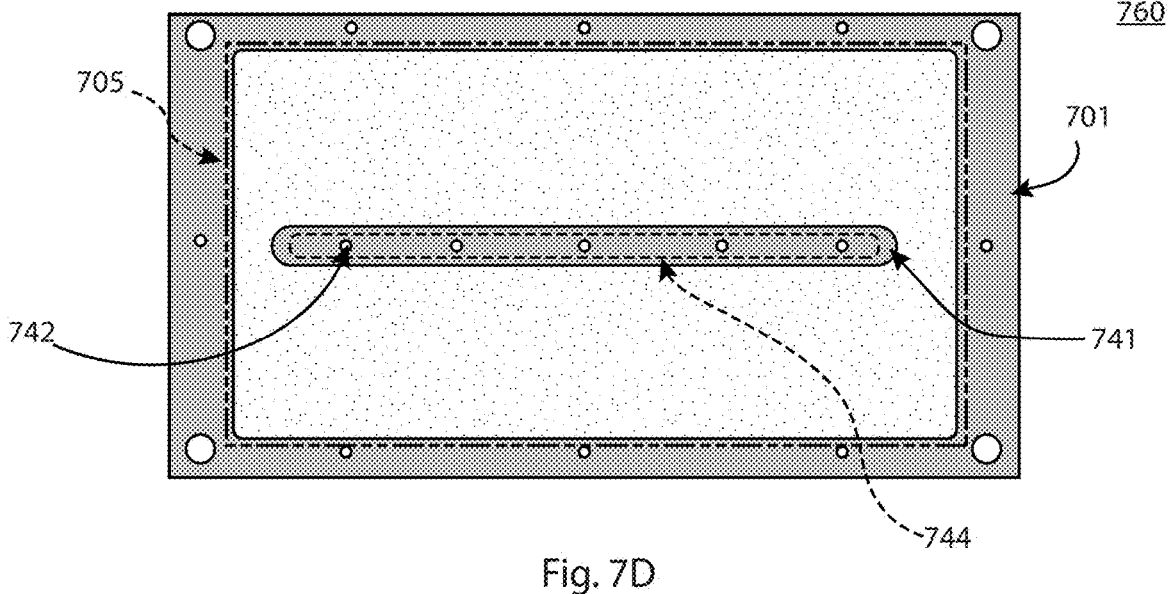
FIG. 7D shows a filter membrane in accordance with an embodiment of the invention.

FIGS. 7A-D shows a filter membranes in accordance with an embodiment of the invention. The filter membrane 700 includes a pore region 702 and holes 704 for attaching to standoffs of the filter assembly. Support holes 703 may be found in the non-porous region 701 of the filter membrane 700. A seal such as an O-ring may be placed in region 705 when the filter membrane is placed within the filter assembly. FIG. 7B shows another filter membrane 720 having support regions 721 within the porous region 702. The support regions 721 have holes 723. The support regions 721 allow for placement of seals, such as an O-ring, within region 722. FIG. 7C shows a filter membrane 740 with several holes 742 provided within a single seal region 741. Each hole may include a seal, such as an O-ring, within region 741. FIG. 7D shows another examples of a membrane filter 760 which shows that a single seal may be provided within seal region 744 and surround several holes 742 within the seal region 741.

Other embodiments and uses of the invention will be apparent to those skilled in the art from consideration of the specification and practice of the invention disclosed herein. All references cited herein, including all U.S. and foreign patents and patent applications, are specifically and entirely hereby incorporated herein by reference. It is intended that the specification and examples be considered exemplary only, with the true scope and spirit of the invention indicated by the following claims

What is claimed is:

1. A perfusion filter assembly comprising:
a plurality of standoffs, the plurality of standoffs positioned on a bottom surface;
a filter holding device adapted to engage the plurality of standoffs;
a filter membrane, the filter membrane comprising:
a porous filter region, the porous filter region comprising a plurality of pores having a pore dimension within a range of 20 nm and less than 100 microns; and
a membrane frame region surrounding the porous filter region, where the membrane frame region comprises a plurality of openings adapted to engage the plurality of standoffs;
a seal abutting the filter membrane; and
a support frame adapted to engage with the filter holding device and the plurality of standoffs and secure the filter membrane and the seal between the filter holding device and the support frame, the filter membrane being spaced from the bottom surface by way of the plurality of standoffs.

2. The perfusion filter assembly of claim 1, wherein the filter membrane further comprises a support region having a plurality of membrane support holes, the membrane support holes having a minimum dimension greater than the pore dimension.

3. The perfusion filter assembly of claim 1, wherein the membrane frame region is of the same material as the porous filter region with a different thickness.

4. The perfusion filter assembly of claim 1, wherein the membrane frame region is of a different material than the membrane filter.

5. The perfusion filter assembly of claim 1, wherein the membrane frame region comprises a plurality of frame support holes.

6. The perfusion filter assembly of claim 2, wherein the support frame and the filter holding device are engaged with each other by bonding wherein the support frame and filter holding device include a recessed region for engaging with the support region of the filter membrane and securing the filter membrane within the filter assembly.

7. The perfusion filter assembly of claim 1, wherein the filter membrane is a polyimide filter membrane.

8. A flexible bag bioreactor comprising:
an inner surface and an outer surface;
a perfusion filter assembly, the perfusion filter assembly comprising:
a plurality of standoffs;
a filter holding device adapted to engage the plurality of standoffs;
a filter membrane, the filter membrane comprising:
a porous filter region, the porous filter region comprising a plurality of pores having a pore dimension within a range of 20 nm and less than 100 microns; and
a membrane frame region surrounding the porous filter region,
where the membrane frame region comprises a plurality of openings adapted to engage the plurality of standoffs;
a seal abutting the filter membrane; and
a support frame adapted to engage with the filter holding device and the plurality of standoffs and secure the filter membrane and the seal between the filter holding device and the support frame within the perfusion filter assembly, wherein the perfusion filter assembly is attached to the inner surface of the flexible bag via the plurality of standoffs such that the filter membrane held by the perfusion filter assembly is provided at least a distance from the inner surface of the flexible bag.

9. The flexible bag bioreactor of claim 8, wherein the filter membrane further comprises a support region having a plurality of membrane support holes, the membrane support holes having a minimum dimension greater than the pore dimension.

10. The flexible bag bioreactor of claim 8, wherein the membrane frame region is of the same material as the porous filter region with a different thickness.

11. The flexible bag bioreactor of claim 8, wherein the membrane frame region is of a different material than the membrane filter.

12. The flexible bag bioreactor of claim 8, wherein the membrane frame region comprises a plurality of frame support holes.

13. The flexible bag bioreactor of claim 9, wherein the support frame and the filter holding device are engaged with each other by bonding wherein the support frame and filter holding device include a recessed region for engaging with the support region of the filter membrane and securing the filter membrane within the filter assembly.

14. The flexible bag bioreactor of claim 8, wherein the filter membrane is a polyimide filter membrane.

\* \* \* \* \*